(12) United States Patent
Kataoka

(10) Patent No.: US 8,306,939 B2
(45) Date of Patent: Nov. 6, 2012

(54) EXAMINATION VALUE PREDICTING DEVICE USING ELECTROPHORESIS WAVEFORM, PREDICTION METHOD, AND PREDICTING PROGRAM

(75) Inventor: Hiromi Kataoka, Nankoku (JP)

(73) Assignee: Kochi University, Kochi (JP)

( * ) Notice: Subject to any disclaimer, the term of this patent is extended or adjusted under 35 U.S.C. 154(b) by 672 days.

(21) Appl. No.: 12/450,016

(22) PCT Filed: Mar. 10, 2008

(86) PCT No.: PCT/JP2008/054326
§ 371 (c)(1),
(2), (4) Date: Sep. 8, 2009

(87) PCT Pub. No.: WO2008/111566
PCT Pub. Date: Sep. 18, 2008

(65) Prior Publication Data
US 2010/0036791 A1 Feb. 11, 2010

(30) Foreign Application Priority Data

Mar. 12, 2007 (JP) .................................. 2007-61704

(51) Int. Cl.
*G06F 9/44* (2006.01)
*G06N 7/02* (2006.01)
*G06N 7/06* (2006.01)
(52) U.S. Cl. ........................................................ 706/52
(58) Field of Classification Search ........................ None
See application file for complete search history.

(56) References Cited

U.S. PATENT DOCUMENTS 5,922,184 A * 7/1999 Binder et al. ................. 204/452
5,932,080 A * 8/1999 Likuski ........................ 204/451

FOREIGN PATENT DOCUMENTS

| JP | H06-241986 A | 9/1994 |
|----|--------------|--------|
| JP | 2001-74694 A | 3/2001 |
| JP | 2007-139548 A | 6/2007 |

OTHER PUBLICATIONS

Roldan-Assad et al. "Capillary zone electrophoretic determination of C2-C18 linear saturated free fatty acids with indirect absorbance detection", Journal of Chromatography A, 708 (1995) pp. 339-350.*

(Continued)

*Primary Examiner* — Alan Chen
*Assistant Examiner* — Li-Wu Chang
(74) *Attorney, Agent, or Firm* — Posz Law Group, PLC

(57) ABSTRACT

Electrophoresis waveform data and a prediction equation for predicting the amount of a substance in an analyte or the presence of a disease in the living body from which the analyte was obtained are recorded. The prediction equation is a regression equation in which the explanatory variable is an absorbance value corresponding to a mobility in corrected waveform data generated as a result of electrophoresis waveform data on a plurality of analytes, and the criterion variable is the amount of the substance or the presence of a disease. The test value prediction method includes a step of generating corrected waveform data by performing normalization and area correction on the electrophoresis waveform data recorded in the recording unit, and a step of calculating a prediction value of the amount of the specific substance by substituting the absorbance value from the mobility, with an absorbance value from the corrected waveform data.

13 Claims, 14 Drawing Sheets

OTHER PUBLICATIONS

"How to use a protein assay standard curve", http://www.piercenet.com/files/TR0057-Read-std-curves.pdf, 2007, pp. 4.*

H. Kataoka, "Doteki Keikakuho—SOM ni Motozuku Ruiji Hakei Kensaku System (A Similarity Wave Data Search Based on Dynamic Programming—SOM)," *Transactions of Information Processing Society of Japan*, Sep. 15, 2001, vol. 42, No. SIG10 (TOD11), pp. 92-99 (English abstract enclosed).

H. Kataoka, et al., "Pattern Hakken no tame no Han'yoteki na Chromatography Idodo Seikika Algorithm no Kaihatsu (Development of versatile algorithm for normalization of mobility in chromatography for pattern discovery)," *Japanese Journal of Clinical Laboratory Automation*, Dai 37 Kai Taikai Shorokushu, Sep. 1, 2005, vol. 30, No. 4 (whole No. 161), p. 548 (Discussed on p. 3 of specification).

H. Kataoka, et al., "Seido Hosho no Kongo no Tenkai (Future Evolution of Accuracy Assurance)," *The Japanese Journal of Clinical Pathology*, Sep. 25, 1999, vol. 47, No. 9, pp. 823-829 (English abstract enclosed) (Discussed on p. 3 of specification).

International Search Report mailed on Apr. 22, 2008 for the corresponding International patent application No. PCT/JP2008/054326 (English translation enclosed).

* cited by examiner

| Order | Variable Name | Regression Coefficient |
|---|---|---|
| 0 | | 5.355015 |
| 1 | Sex | -0.035154 |
| 2 | Age | -0.004319 |
| 3 | P20 | -0.006222 |
| 4 | P22 | 0.008782 |
| 5 | P81 | -0.010052 |
| 6 | P83 | 0.013883 |
| 7 | P89 | -0.005158 |
| 8 | P97 | 0.004236 |
| 9 | P125 | -0.001469 |
| 10 | P127 | 0.001714 |
| 11 | P146 | -9.56E-05 |
| 12 | P163 | 1.81E-04 |
| 13 | P166 | -4.56E-04 |
| 14 | P179 | 0.001077 |
| 15 | P212 | -0.012188 |
| 16 | P213 | 0.012182 |
| 17 | P235 | -7.04E-04 |
| 18 | P257 | -0.001033 |
| 19 | P289 | 4.16E-04 |
| 20 | P350 | 0.004908 |
| 21 | P353 | -0.003991 |
| 22 | P365 | 2.88E-04 |
| 23 | P380 | 1.48E-04 |
| 24 | P432 | 0.002295 |
| 25 | P433 | -0.003441 |
| 26 | P436 | 0.00107 |
| 27 | P467 | 0.001779 |
| 28 | P468 | -0.004112 |
| 29 | P469 | 0.002071 |

Fig.12

| Order | Variable Name | Regression Coefficient |
|---|---|---|
| 0 |  | 64.12195 |
| 1 | Sex | 4.296813 |
| 2 | Age | −0.069401 |
| 3 | P15 | 0.080641 |
| 4 | P58 | −0.182437 |
| 5 | P59 | 0.202341 |
| 6 | P76 | 0.091854 |
| 7 | P100 | −0.062258 |
| 8 | P119 | 0.009701 |
| 9 | P144 | 0.001623 |
| 10 | P151 | −0.003038 |
| 11 | P157 | 0.002034 |
| 12 | P179 | −0.182207 |
| 13 | P180 | 0.280311 |
| 14 | P216 | 0.047429 |
| 15 | P221 | −0.0459 |
| 16 | P241 | −0.012322 |
| 17 | P258 | −0.072827 |
| 18 | P261 | 0.10866 |
| 19 | P271 | −0.162631 |
| 20 | P272 | 0.160493 |
| 21 | P300 | −0.02029 |
| 22 | P303 | 0.033827 |
| 23 | P321 | 0.019594 |
| 24 | P330 | 0.069924 |
| 25 | P332 | −0.07193 |
| 26 | P335 | 0.061617 |
| 27 | P342 | −0.082826 |
| 28 | P343 | 0.094422 |
| 29 | P358 | 0.021809 |
| 30 | P362 | −0.011503 |
| 31 | P387 | −0.006567 |
| 32 | P404 | −0.001395 |
| 33 | P424 | −0.001924 |
| 34 | P440 | 0.01005 |
| 35 | P441 | −0.02561 |
| 36 | P442 | 0.018675 |
| 37 | P444 | −0.004679 |
| 38 | P452 | 0.015102 |
| 39 | P453 | −0.016159 |
| 40 | P472 | −0.001245 |
| 41 | P495 | −0.00805 |

US 8,306,939 B2

EXAMINATION VALUE PREDICTING DEVICE USING ELECTROPHORESIS WAVEFORM, PREDICTION METHOD, AND PREDICTING PROGRAM

TECHNICAL FIELD

The present invention relates to a test value prediction apparatus, a test value prediction method, and a test value predicting program in which electrophoresis waveform data is used, which are capable of accurately predicting the amount of a specific substance, particularly the amount of a substance to be measured in a biopsy (i.e., a test item), and the presence or absence of a disease, using waveform information that was obtained from the measurement of an electrophoresis waveform, particularly an electrophoresis test, and normalized. Note that the present invention not only estimates a test value at the time of measurement of the electrophoresis waveform but can also estimate how the test value changes over time after the measurement, and thus the term "estimation" is also described as "predication" in this specification.

BACKGROUND ART

In medical institutions, diagnosis based on laboratory test values usually uses test values from a plurality of test items. For example, for a health examination of metabolic syndrome, a plurality of test items having relatively high specificity for the syndrome, such as neutral fat, HDL cholesterol, LDL cholesterol, and hemoglobin A1c, are simultaneously tested, and the doctors use the obtained test values for diagnosis. Currently in Japan, the cost of testing in terms of the National Health Insurance point scheme is a simplified total of 1,859 points per diagnosis. Additionally, due to the analytical principles of these test items being different from one another, medical institutions and test institutions have and maintain a plurality of analysis equipment.

A protein fractionation test is known as a method to analyze waveform information obtained by an electrophoresis method used for laboratory tests and genetic analysis. A method of specifying substances separated by mobility is employed for the analysis of waveform information obtained by electrophoresis used for laboratory tests, genetic analyses, and the like. Since mobility varies depending on various analytical conditions, it is necessary to normalize the mobility, i.e., to correct the time axis, for such an analysis. Methods for normalizing the mobility that have been used include a method of mixing a reference marker substance into a sample and a method of correcting the mobility using a characteristic waveform peak or the like as an index.

In the case of serum protein electrophoretic analysis, for example, a plurality of samples can be analyzed simultaneously by applying several tens of samples to one film sheet of cellulose acetate. Therefore, according to a method for correcting the mobility in the sheet (see Non-Patent Document 1 listed below) invented by the present inventor, a monitoring sample whose mobility has been examined is mixed into analysis samples, and thereby all the mobilities can be corrected based on the mobility of the monitoring sample. With regard to capillary zone electrophoresis, an estimation method that uses theoretical mobility is known (see Patent Document 1 listed below).

Further, a method of normalizing a mobility measured without mixing a marker substance into a sample has been suggested by the present inventor (see Non-patent Document 2 listed below).

[Patent Document 1] Japanese Unexamined Patent Publication No. 2001-074694
[Non-Patent Document 1] Hiromi KATAOKA, Masahide SASAKI, Hideaki NISHIDA, Kyoko TAKEDA, and Tetsuro SUGIURA: "*Seido Hosho no Kongono Tenkai* (Future Evolution of Accuracy Assurance), *Rinshou Byouri* (Clinical Pathology), 47(9), pp. 823-829, 1999.
[Non-patent Document 2] Hiromi KATAOKA, Kiyoshi ICHIHARA, Kanako TAKAHASHI, Kuniaki SAITO, Taisuke HISAHARA, Katsumi Ogura, Tetsuro SUGIURA: *Pattern hakken no tameno hannyotekina chromatography idodo seikika algorithm no kaihatsu* (Development of versatile algorithm for normalization of mobility in chromatography for pattern discovery), Japan Society for Clinical Laboratory Automation, collection of abstracts of the 37th Conference, p. 548.

DISCLOSURE OF INVENTION

Technical Problem

As described above, conventional diagnosis based on laboratory test values has a problem, i.e., the cost of testing charged to the individual is high (about 15,000 yen).

Medical institutions and test institutions face a problem of heavy expenditures for capital investment in analysis equipment, reagents, manpower, etc.

At the same time, with the conventional protein fractionation test, a specific substance cannot be clearly separated based on the area of a distinctly fractionated waveform and a subtle difference in its pattern. Although the protein fractionation test is sometime used to diagnose a disease based on the waveform pattern, only about 5 disease groups can be diagnosed.

In order to solve the above described problems, a purpose of the present invention is to provide a test value prediction apparatus, a test value prediction method, and a test value predicting program, capable of accurately predicting the amount of a specific substance, the presence or absence of a disease, and the like, using waveform information obtained from an electrophoresis test and normalized.

Technical Solution

The present inventor conducted extensive research to solve the above problems. As a result, the present inventor has found that the waveform pattern in the vicinity of albumin in diabetic patients tends to be different from that in healthy individuals although it has been considered that diabetes cannot be diagnosed using the protein fractionation test. The present invention is accomplished based on this finding.

A test value prediction apparatus (1) according to the present invention, includes a recording unit and an operation unit, wherein
 a mobility and an absorbance value corresponding to the mobility are used as a set of paired data; and
 electrophoresis waveform data formed by a plurality of said sets of paired data, and a prediction equation for predicting the amount of a specific substance in an analyte or the presence or absence of a disease in the living body from which the analyte was obtained are recorded in the recording unit;
 the prediction equation is a regression equation predetermined by a maximum likelihood estimation method, in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;

the operation unit is configured to
read the electrophoresis waveform data recorded in the recording unit, and generate corrected waveform data by performing normalization and area correction on the electrophoresis waveform data, and read the prediction equation recorded in the recording unit, calculate a value of the prediction equation by substituting the absorbance value corresponding to the mobility which is the explanatory variable of the prediction equation with an absorbance value from the corrected waveform data generated from the electrophoresis waveform data recorded in the recording unit, and use the calculated value as a prediction value of the amount of the specific substance or the presence or absence of a disease; and the area correction is a process to correct absorbance values in electrophoresis waveform data using the area in the normalized electrophoresis waveform data and the total protein value of the analyte.

Further, a test value prediction apparatus (2) according to the present invention is the test value prediction apparatus (1) defined above, wherein the specific substance is one substance selected from the group consisting of hemoglobin A1c, glycoalbumin, HDL cholesterol, LDL cholesterol, total cholesterol, triglyceride, AFP, CEA, ALB, C4, transferrin, CRP, IgA, IgG, IgM, TP, CHE, GLB, ZTT, serum Ca, Na in urine, RBC, HT, HB, blood sedimentation, glucose in 24-hour collected urine, protein in 24-hour collected urine, 1.5-AG, anti-GAD Ab, circadian sugar level, blood sugar during glucose tolerance test (each hourly value), insulin during glucose tolerance test (each hourly value), lactate, pyruvic acid, sialic acid, hyaluronic acid, E-CHO, NEFA, H-CHO, TIBC, serum copper, zinc, vitamin B1, RBP, LCAT, lysozyme, CKMB (MB %, MM %), LH, FSH, prolactin, ACTH, T3, T4, CPR, insulin, BNP-FEI, FIB, lupus anti core grant, ASK, CH50, C3, LE, thyroid, anti-TG, anti-TPO, haptoglon, SAA, IAP, B2-MIC, NSE, HGF, P-3-P, collagen 7S, CA19-9R, CA72-4, BCA225, STN, pro-GRP, TPA, ELASTA, SPAN1, ICTP, PSA, ICG, ALB in urine, NAG in urine, and nasal fluid eosinophils.

Further, a test value prediction apparatus (3) according to the present invention is the test value prediction apparatus (1) defined above, wherein the corrected waveform data used for determination of the prediction equation is waveform data obtained by performing convolution using Gaussian distribution on waveform data generated as a result of normalization of the electrophoresis waveform data on a plurality of analytes; and the operation unit normalizes the electrophoresis waveform data recorded in the recording unit, performs convolution using Gaussian distribution on the normalized waveform data, and generates the corrected waveform data used for calculation of the prediction value.

Further, a test value prediction apparatus (4) according to the present invention is the test value prediction apparatus (1) defined above, wherein the specific substance is CEA; and the amount of the specific substance used as a criterion variable for determination of the prediction equation is a logarithmic value of a measured value of CEA.

Further, a test value prediction apparatus (5) according to the present invention is the test value prediction apparatus (1) defined above, wherein the recording unit further records a first parameter and a second parameter that are used for normalization;

the operation unit normalizes the electrophoresis waveform data using a linear function in which the first parameter is a slope and the second parameter is an intercept;

a plurality of warping functions that convert the electrophoresis waveform data into a plurality of reference waveform data, and DTW distances corresponding the plurality of warping functions are obtained, and the first parameter is the slope of a straight line approximating the warping function that corresponds to the minimum DTW distance among the plurality of DTW distances, and the second parameter is the intercept of the straight line; and the slope of the straight line approximating the warping function is obtained by
calculating slopes between any folding points of the warping function,
excluding slopes included in predetermined regions at both ends when the plurality of slopes between folding points are arranged in order of value,
obtaining the slope of the straight line from the remaining slopes.

A test value prediction apparatus (6) according to the present invention is the test value prediction apparatus (1) defined above, wherein when the corrected waveform data is generated such that the albumin peak is at position 149 and the marker peak is at position 396, a prediction equation for hemoglobin A1c contains, as explanatory variables, absorbance values corresponding to mobilities at least at positions 28, 130, 138, 148, 258, 261, 302, 329, and 419, a prediction equation for HDL cholesterol contains, as an explanatory variable, an absorbance value corresponding to a mobility at least at position 189, or a prediction equation for glycoalbumin contains, as explanatory variables, absorbance values corresponding to mobilities at least at positions 27, 28, 31, 128, 150, 346, and 347.

Further, a test value predicting method (1) according to the present invention is a method for predicting the amount of a specific substance in an analyte or the presence or absence of a disease in the living body from which the analyte was obtained, by using a computer including a recording unit and an operation unit, wherein a mobility and an absorbance value corresponding to the mobility are used as a set of paired data; and electrophoresis waveform data formed by a plurality of said sets of paired data, and a prediction equation for predicting the amount of a specific substance in an analyte or the presence or absence of a disease in the living body from which the analyte was obtained are recorded in the recording unit;

the prediction equation is a regression equation predetermined by maximum likelihood estimation method in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;

the test value prediction method further including a first step in which the operation unit reads the electrophoresis waveform data recorded in the recording unit, and generates corrected waveform data by performing normalization and area correction on the electrophoresis waveform data, and a second step in which the operation unit reads the prediction equation recorded in the recording unit, calculates a value of the prediction equation by substituting the absorbance value corresponding to the mobility which is the explanatory variable of the prediction equation, with an absorbance value from the corrected waveform data generated from the electrophoresis waveform data recorded in the recording unit, and uses the calculated value as a prediction value of the amount of the specific substance or the presence or absence of a disease; and the area correction is a process to correct absorbance values in electrophoresis waveform data using the area in the normalized electrophoresis waveform data and the total protein value of the analyte.

Further, a test value prediction method (2) according to the present invention is the test value prediction method (1) defined above, wherein the specific substance is one substance selected from the group consisting of hemoglobin A1c, glycoalbumin, HDL cholesterol, LDL cholesterol, total cholesterol, triglyceride, AFP, CEA, ALB, C4, transferrin, CRP, IgA, IgG, IgM, TP, CHE, GLB, ZTT, serum Ca, Na in urine, RBC, HT, HB, blood sedimentation, glucose in 24-hour collected urine, protein in 24-hour collected urine, 1.5-AG, anti-GAD Ab, circadian sugar level, blood sugar during glucose tolerance test (each hourly value), insulin during glucose tolerance test (each hourly value), lactate, pyruvic acid, sialic acid, hyaluronic acid, E-CHO, NEFA, H-CHO, TIBC, serum copper, zinc, vitamin B1, RBP, LCAT, lysozyme, CKMB (MB %, MM %), LH, FSH, prolactin, ACTH, T3, T4, CPR, insulin, BNP-FEI, FIB, lupus anti core grant, ASK, CH50, C3, LE, thyroid, anti-TG, anti-TPO, haptoglon, SAA, IAP, B2-MIC, NSE, HGF, P-3-P, collagen 7S, CA19-9R, CA72-4, BCA225, STN, pro-GRP, TPA, ELASTA, SPAN1, ICTP, PSA, ICG, ALB in urine, NAG in urine, and nasal fluid eosinophils.

Further, a test value prediction method (3) according to the present invention is the test value prediction method (1) defined above, wherein the corrected waveform data used for determination of the prediction equation is waveform data obtained by performing convolution using Gaussian distribution on waveform data generated as a result of normalization of the electrophoresis waveform data on a plurality of analytes; and in the second step, the operation unit normalizes the electrophoresis waveform data recorded in the recording unit, performs convolution using Gaussian distribution on the normalized wave form data, and generates the corrected waveform data used for calculation of the prediction value.

Further, a test value prediction method (4) according to the present invention is the test value prediction method (1) defined above, wherein the specific substance is CEA; and the amount of the specific substance used as the criterion variable for determination of the prediction equation is a logarithmic value of a measured value of CEA.

Further, a test value prediction method (5) according to the present invention is the test value prediction method (1) defined above, wherein the recording unit further records a first parameter and a second parameter that are used for normalization;

in the first step, the operation unit normalizes the electrophoresis waveform data using a linear function in which the first parameter is a slope and the second parameter is an intercept;

a plurality of warping functions that convert the electrophoresis waveform data into a plurality of reference waveform data, and DTW distances corresponding the plurality of warping functions are obtained, and the first parameter is the slope of a straight line approximating the warping function that corresponds to the minimum DTW distance among the plurality of DTW distances, and the second parameter is the intercept of the straight line; and the slope of the straight line approximating the warping function is obtained by calculating slopes between any folding points of the warping function, excluding slopes included in predetermined regions at both ends when the plurality of slopes between folding points are arranged in order of value, obtaining the slope of the straight line from the remaining slopes.

A test value prediction method (6) according to the present invention is the test value prediction method (1) defined above, wherein when the corrected waveform data is generated such that the albumin peak is at position 149 and the marker peak is at position 396, a prediction equation for hemoglobin A1c contains, as explanatory variables, absorbance values corresponding to mobilities at least at positions 28, 130, 138, 148, 258, 261, 302, 329, and 419, a prediction equation for HDL cholesterol contains, as an explanatory variable, an absorbance value corresponding to a mobility at least at position 189, or a prediction equation for glycoalbumin contains, as explanatory variables, absorbance values corresponding to mobilities at least at positions 27, 28, 31, 128, 150, 346, and 347.

Further, a test value prediction program according to the present invention is a program for causing a computer including a recording unit and an operation unit to predict the amount of a specific substance in an analyte or the presence or absence of a disease in the living body from which the analyte was obtained, wherein a mobility and an absorbance value corresponding to the mobility are used as a set of paired data; and electrophoresis waveform data formed by a plurality of said sets of paired data, and a prediction equation for predicting the amount of a specific substance in an analyte or the presence or absence of a disease in the living body from which the analyte was obtained are recorded in the recording unit;

the prediction equation is a regression equation predetermined by maximum likelihood estimation method in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;

the test value prediction program enabling a first function in which the operation unit is caused to read the electrophoresis waveform data recorded in the recording unit and generate corrected waveform data by performing normalization and area correction on the electrophoresis waveform data, and a second function in which the operation unit is caused to read the prediction equation recorded in the recording unit, calculate a value of the prediction equation by substituting the absorbance value corresponding to the mobility which is the explanatory variable of the prediction equation with an absorbance value from the corrected waveform data generated from the electrophoresis waveform data recorded in the recording unit, and use the calculated value as a prediction value of the amount of the specific substance; and the area correction is a process to correct absorbance values in electrophoresis waveform data using the area in the normalized electrophoresis waveform data and the total protein value of the analyte.

Advantageous Effects

The present invention enables calculation of the amount of a substance (test value) or determination of the presence or absence of a disease (test value) with high accuracy, either of which could not be predicted by a conventional protein fractionation test, by using a regression equation determined using the maximum likelihood estimation method (such as multiple regression analysis, multiple logistic regression analysis, etc.) in which the normalized electrophoresis waveform data is used as an explanatory variable.

Various test values are predicted simply by performing a protein fractionation test, which is a relatively inexpensive test, before performing a plurality of tests that impose high costs on a test subject, e.g., a patient, thus limiting the expenses imposed on a test subject who does not need to undergo various tests. The protein fractionation test used in the present invention counts for only 19 points under the National Health Insurance point scheme in Japan.

When a predicted value is deviated from a standard value (healthy range), an actual test can be performed according to need, thus reducing the frequency at which tests are performed. Accordingly, this reduces the number of test apparatuses used in medical institutions and test institutions, and also reduces the related cost for capital investment, reagents, labor, etc. The protein fractionation test used in the present invention is a test that can be analyzed as long as an electrophoresis apparatus is used exclusively for the test.

Further, the present invention is not limited to application in the protein fractionation test. Application of the present invention to data such as response curve data during an analysis of laboratory tests enables the obtainment of prediction values of various test items by a single analysis, and thus it is possible to construct a diagnosis support system capable of quickly and efficiently providing information to a test subject.

BRIEF DESCRIPTION OF DRAWINGS

FIG. 12 is a drawing showing regression coefficients in a table form, which were determined for HDL in accordance with the flowchart in FIG. 3.

EXPLANATION OF REFERENCE SYMBOLS

Figure 1:
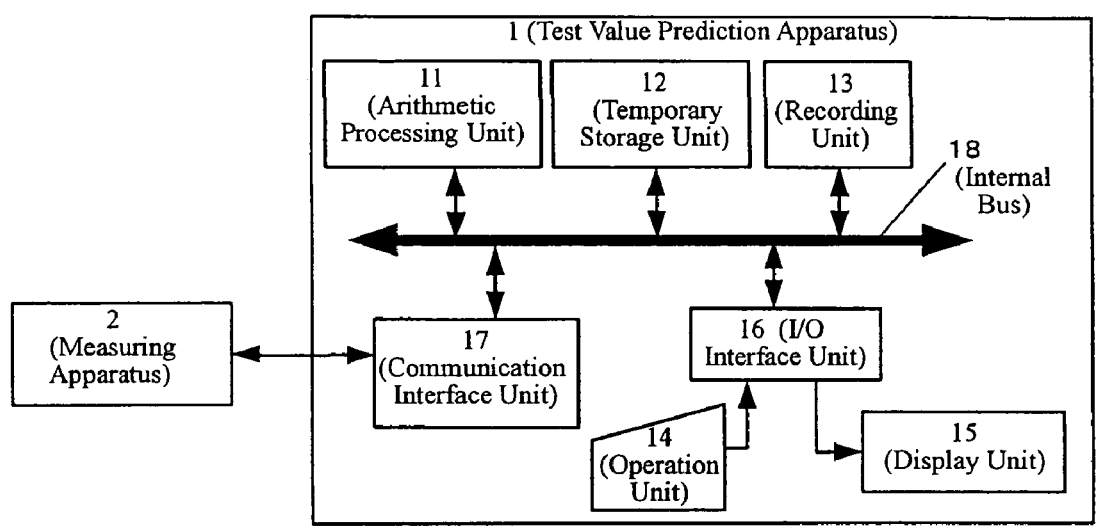
FIG. 1 is a block diagram showing the schematic configuration of a test value prediction apparatus according to an embodiment of the present invention.

1 Test value prediction apparatus
11 Arithmetic processing unit
12 Temporary storage unit
13 Recording unit
14 Operation unit
15 Display unit
16 I/O interface unit
17 Communication interface unit
18 Internal bus
2 Measuring apparatus

BEST MODE FOR CARRYING OUT THE INVENTION

An embodiment of the present invention will hereinafter be described with reference to the attached drawings.

FIG. 1 is a block diagram showing the schematic configuration of a test value prediction apparatus that uses electrophoresis waveform according to an embodiment of the present invention. A test value prediction apparatus 1 according to the present invention includes an arithmetic processing unit 11; a temporary storage unit 12; a recording unit 13; an operation unit 14 that provides instructions and inputs data to the arithmetic processing unit 11; a display unit 15 that displays processing results from the arithmetic processing unit 11; an interface unit (hereinafter referred to as an "I/O IF unit") 16 for interfacing with the operation unit 14 and the display unit 15; a communication interface unit (hereinafter referred to as "communication IF unit") 17 that exchanges data with an external measuring apparatus 2; and an internal bus 18 for exchanging data among the internal units. The measuring apparatus 2 is, for example, a capillary zone electrophoresis apparatus.

When the test value prediction apparatus 1 is constructed using, for example, a computer, the arithmetic processing unit 11, the temporary storage unit 12, and the recording unit 13 may be a CPU, an RAM, and a hard disk, respectively. The operation unit 14 may be a keyboard, a mouse, or a touch panel. The I/O IF unit 16 may be a serial or parallel interface compatible with the operation unit 14. The I/O IF unit 16 has a video memory and a digital-to-analog converter, and outputs an analog signal in accordance with the video format of the display unit 15, whereby an image for presenting information is displayed on the display unit 15.

Figure 2:
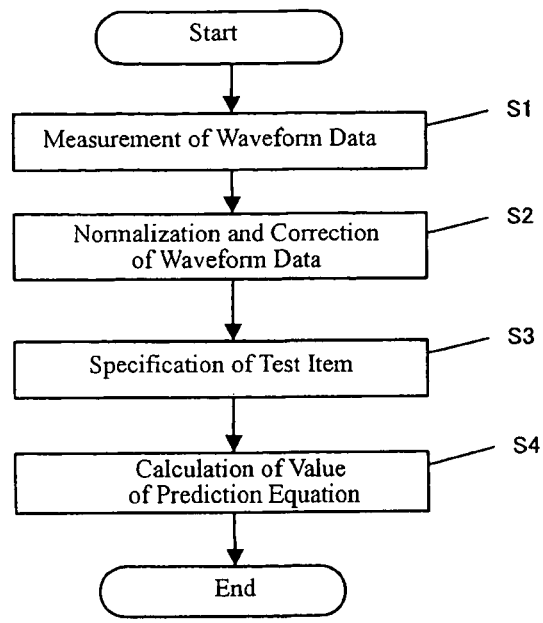
FIG. 2 is a flowchart showing the process to calculate a prediction value using a prediction equation, which is one of the processes performed by the test value prediction apparatus according to the embodiment of the present invention.
Figure 3:
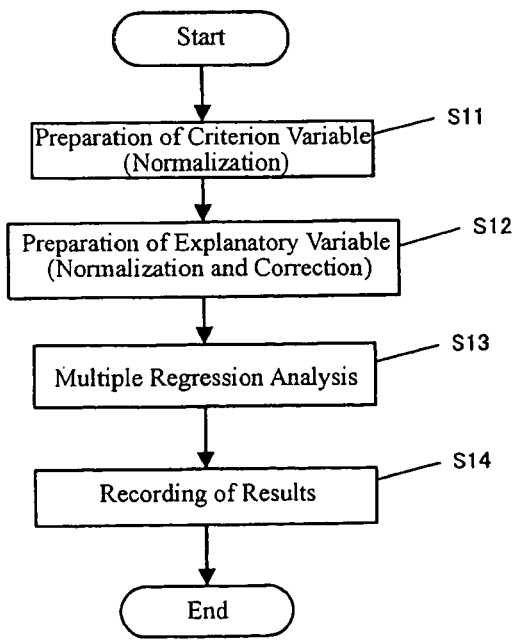
FIG. 3 is a flowchart showing the process to determine a prediction equation, which is one of the processes performed by the test value prediction apparatus according to the embodiment of the present invention.

FIGS. 2 and 3 are flowcharts showing the operation of the test value prediction apparatus 1 according to the embodiment. The operation of the test value prediction apparatus 1 will be described in detail below with reference to FIGS. 2 and 3. The following processes are explained as being performed by the arithmetic processing unit 11 of the test value prediction apparatus 1, unless otherwise specified. The arithmetic processing unit 11 performs predetermined processing by acquiring data inputted through an operation of the operation unit 14, recording the data in the recording unit 13, reading the data from the recording unit 13 into the temporary storage unit 12 as required, performing predetermined processing, and subsequently recording the results in the recording unit 13. The arithmetic processing unit 11 also creates screen data for prompting the operation of the operation unit 14 and for displaying the processing results, and displays these images on the display unit 15 via the video RAM of the I/O IF unit 16. Additionally, results (hereinafter also referred to as test values) obtained by testing a plurality of analytes (biological samples such as blood extracted from test subjects) for predetermined test items (hemoglobin A1c, HDL cholesterol, etc.) are recorded in the recording unit 13 in a manner such that the results are associated with information that specifies an analyte (for example, a code number for each analyte) and information that specifies a test item (for example, a code number of each test item). In other words, analytes, test items, and test results of a group of analytes are recorded such that the relationship there among is evident.

Calculation of Prediction Value

First, in Step S1, the arithmetic processing unit 11 acquires measurement data from the measuring apparatus (electrophoresis apparatus) 2 via the communication IF unit 17 and records the data in the recording unit 13. The measurement data is waveform data on mobilities for a specific analyte, and is one-dimensional time series data measured at specific time intervals.

Figure 4:
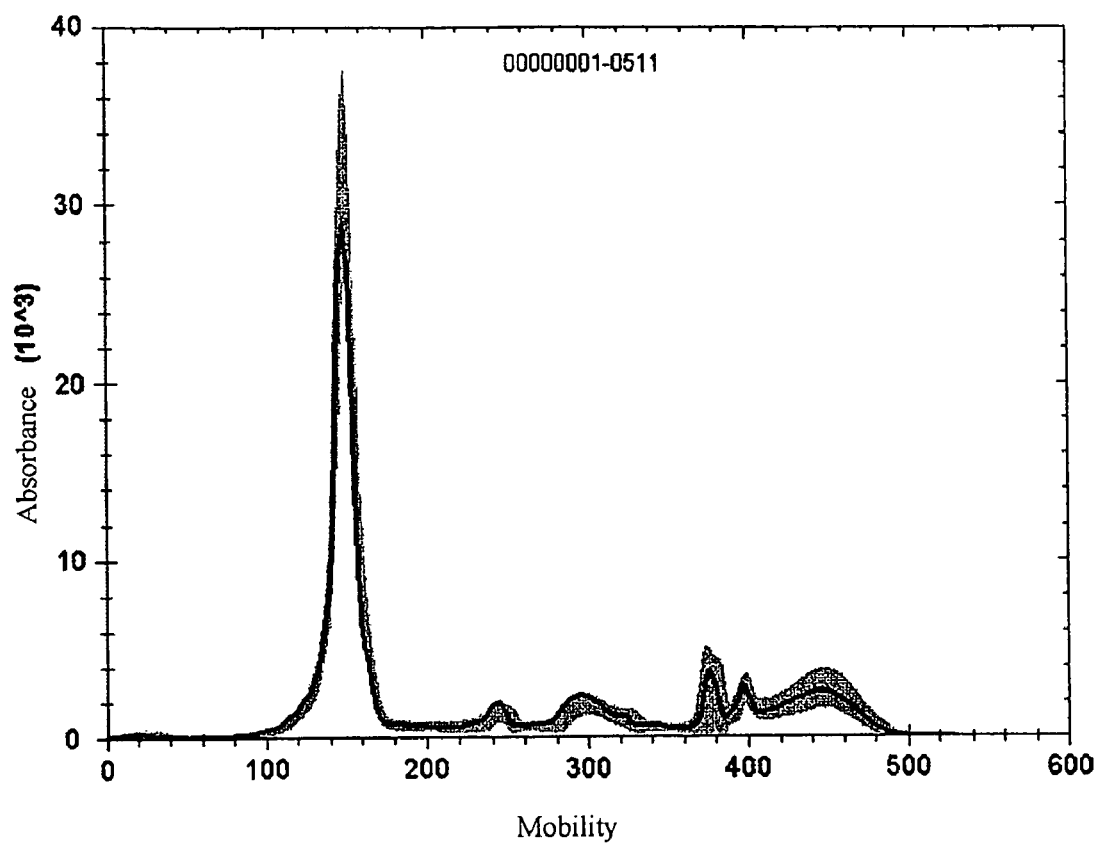
FIG. 4 is a graph showing an example of waveform data of mobilities.

In Step S2, the arithmetic processing unit 11 performs normalization and area correction on the obtained measurement waveform data. A normalization method may be a conventional method described in the section "Background Art" above or a later described method. FIG. 4 shows an example of waveform data that was subjected to normalization and area correction. In FIG. 4, the horizontal axis indicates the normalized mobility and the vertical axis indicates the absorbance after the area was corrected. The mobilities are indicated with integers from 1 to 500. Note that, in FIG. 4, normalized waveform data is represented by a solid line, and the shadows on the background indicate a range of standard values obtained in a healthy population.

The area correction is a process to calculate a value of each point of the normalized waveform (mobilities are in a range of 1 to 500) using an equation of Simpson's rule for definite integrals, and correct the area of the waveform such that the area is $1 \times 10^6$ when the total protein value is 7.0 (g/dl). In other words, the height of the normalized waveform (absorbance after area correction) is calculated using the total protein value of the analyte by the following equations:

$$\text{correction factor} = \text{total protein value} \times 1 \times 10^6 / 7.0 \times \text{area},$$

$$\text{height of normalized waveform} = \text{absorbance before area correction} \times \text{correction factor}.$$

The case in which a correction factor for correcting absorbance values is determined using the area is described herein, but the present invention is not limited to the above method. It suffices insofar as a correction factor enables correction of an absorbance value such that the measured absorbance value does not fall too far out of a predetermined range.

In Step S3, the arithmetic processing unit 11 accepts, via the operation unit 14, a specification of a test item subjected to the calculation of a prediction value. The test item is specified by the following method, for example: a list of a plurality of test items of which values are predictable is displayed on the display unit 15, and the operation unit 14 is operated to allow specifying any test item among the displayed test items.

In Step S4, the arithmetic processing unit 11 reads, from the recording unit, a prediction equation corresponding to the test item specified in Step S3, and calculates a value of the prediction equation using the waveform data that was subjected to normalization and area correction in Step S2. Although details are described later, it should be noted that the prediction equation is an equation determined in advance using multiple regression analysis, in which the mobility waveform data on a group of analytes (more accurately, absorbance values corresponding to respective mobilities) is used as an explanatory variable and a test item is used as a criterion variable. The prediction equation is expressed as equation 1.

$$Y = a0 + a1 \times \text{Sex} + a2 \times \text{Age} + \Sigma pi \times Pi \quad \text{(equation 1)}$$

wherein, Y is a test value, Sex is the sex (+1 for male, −1 for female), Age is the age (positive integer value), Pi is a value (absorbance) corresponding to a mobility i of the waveform data, and $\Sigma$ indicates a summation regarding integer value i. Coefficients a1, a2, and pi are regression coefficients determined in advance by multiple regression analysis using Sex, Age, and Pi as explanatory variables. The constant a0 is an intercept. Accordingly, the normalized waveform data obtained in Step S2 is substituted into Pi in equation 1, and the sex and age of the test subject from which the analyte subjected to waveform data measurement was extracted are substituted into Sex and Age, and thereby a value of Y is calculated.

A prediction value (Y) of the test item specified in Step S3 is obtained by the manner described above. Note that when a plurality of test items are specified in Step S3, as long as different prediction equations corresponding to each specified test item have been predetermined in advance, a corresponding prediction equation can be read and a prediction value can be calculated for each specified test item in a similar manner as described above.

In the later described Examples, hemoglobin A1c (herein below also referred to as HbA1c), HDL cholesterol (herein below also referred to as HDL), and glycoalbumin (herein below also referred to as GA) are used as the test items, however, the test items are not limited to the above. For example, the present invention is applicable to the prediction of the following test items: test items relevant to metabolic syndrome such as LDL cholesterol, total cholesterol, and triglyceride; test items relevant to tumor markers such as AFP (α-fetoprotein) and CEA (carcinoembryonic antigen); test items relevant to nutrition management such as ALB (albumin), C4 (complement), and transferrin; and test items relevant to infection and inflammation such as hs-CRP (C-reactive protein), IgA (immunoglobulin A), IgG (immunoglobulin G) and IgM (immunoglobulin M).

Beside those mentioned above, the present invention is applicable to the prediction of values for: TP, CHE, GLB, ZTT, serum Ca, Na in urine, RBC, HT, HB, blood sedimentation, glucose in 24-hour collected urine, protein in 24-hour collected urine, 1.5-AG, anti-GAD Ab, circadian sugar level, blood sugar during glucose tolerance test (each hourly value), insulin during glucose tolerance test (each hourly value), lactate, pyruvic acid, sialic acid, hyaluronic acid, E-CHO, NEFA, H-CHO, TIBC, serum copper, zinc, vitamin B1, RBP, LCAT, lysozyme, CKMB (MB %, MM %), LH, FSH, prolactin, ACTH, T3, T4, CPR, insulin, BNP-FEI, FIB, lupus anti core grant, ASK, CH50, C3, LE, thyroid, anti-TG, anti-TPO, haptoglon, SAA, IAP, B2-MIC, NSE, HGF, P-3-P, collagen 7S, CA19-9R, CA72-4, BCA225, STN, pro-GRP, TPA, ELASTA, SPAN1, ICTP, PSA, ICG, ALB in urine, NAG in urine, nasal fluid eosinophils, etc.

Further, although the above description was directed to a case in which a similar process is performed regardless of the test item subjected to prediction, calculation of some test items may be carried out by performing a convolution operation (convolution integral) on the normalized waveform data using a predetermined function and substituting a value of the resulting waveform data into a prediction equation. For example, it is possible to improve prediction accuracy for CRP (a test item) by using Gaussian distribution to perform a convolution operation on waveform data and using the thus obtained waveform data. CRP is not the only test item for which a convolution operation is preferably used: other test items include, for example, ALB, β2 lipoprotein, C4, transferrin, IAP, IgG, etc.

Because convolution operations are well known in the field of digital signal processing, the explanation thereof is omitted. Note that, in the case of a convolution operation, it is a premise that the determination of a prediction equation by multiple regression analysis (described later) is performed using waveform data on which the same convolution operation has been performed.

Additionally, although the flowchart in FIG. 2 includes a measurement of waveform data, waveform data measured by an apparatus different from the test value prediction apparatus of the present invention may be transmitted to the present test value prediction apparatus via a network and/or a portable recording medium and then subjected to the processes of Step S2 and the following steps.

In addition, although the above description was directed to the case in which the mobilities are indicated with integers from 1 to 500, the range of mobilities is not limited thereto, and neither the lower limit nor the upper limit is limited thereto. It suffices insofar as the mobilities are presented as digital values within a predetermined range and absorbance values corresponding to respective mobilities are provided.

Generation of Prediction Equation

Next, a description is given of a process for generating, by multiple regression analysis, a prediction equation used for the calculation of a prediction value.

In Step S11, in order to prepare criterion variable data, a predetermined test is performed on each analyte j regarding a group of a plurality of analytes j. The arithmetic processing unit 11 records, in the recording unit 13, the test values obtained from the test and multidimensional test values data (waveform) Vj that were subjected to normalization and area correction, in a manner associated with the analytes j. The area correction is the method described in the above section entitled "Calculation of Prediction Value", and a description regarding normalization is given later.

In Step S12, in order to prepare explanatory variable data, waveform data on mobilities is measured for each analyte j using the measuring apparatus (electrophoresis apparatus) 2, regarding the same group of analytes j as described above. Then, the arithmetic processing unit 11 performs normalization and area correction on the waveform data obtained by the measurement, and records, in the recording unit 13, the waveform data that was subjected to normalization and area correction in a manner associated with the analyte j.

In Step S13, the arithmetic processing unit 11 determines regression coefficients (including intercepts) by stepwise multiple regression analysis, using the test values and the wave data collection obtained in Steps S11 and S12, and records the obtained regression coefficients in the recording unit 13. The stepwise multiple regression analysis is a method to determine a combination of significant variables by gradually adding and deleting explanatory variables such that the goodness of fit of the regression equation is the most appropriate. This method is well known to skilled persons in the art, and thus the description thereof is omitted.

A regression equation for a specific test item is obtained using the above described manner. This regression equation is a prediction equation to be used for the above described calculation of a prediction value. Regression coefficients for a plurality of different test items can be obtained using the same group of analytes. When the same group is used, normalization of waveform data in Step S12 needs to be performed only once, but the process in Step S11 needs to be performed for each test item. Further, obtained regression coefficients are recorded in the recording unit 13 in a manner such that these regression coefficients are associated with respective test items.

As described regarding the calculation of a prediction value, calculation for some specific test items may be carried out by performing a convolution operation on normalized waveform data using a predetermined function (for example, Gaussian distribution) and then performing a stepwise multiple regression analysis using the thus obtained waveform data.

Further, for a test item such as CEA in which a test value thereof changes logarithmically according to the worsening of a disease, a prediction equation with improved precision can be generated by calculating the logarithm of such a test value in Step S11 and then performing a stepwise multiple regression analysis using the calculated logarithmic value.

Additionally, although Steps S11 and S12 in FIG. 3 include implementation of a test and measurement of waveform data, respectively, data tested and measured by an apparatus different from the test value prediction apparatus of the present invention may be transmitted to the present test value prediction apparatus via a network and/or a portable recording medium and then subjected to the processes of Step S13 and the following steps.

Further, although the above description was directed to the case in which a stepwise multiple regression analysis is used, there is no limitation thereto. Any multiple regression analysis from which related attributes can be selected may be suitably used. Further, it suffices insofar as the prediction equation is one determined using a method classified as a maximum likelihood estimation method. For example, as described later, when a test value (criterion variable) is binary (for example, the presence or absence of a disease), a multiple logistic regression analysis can be used.

Normalization of Waveform Data

Figure 5:
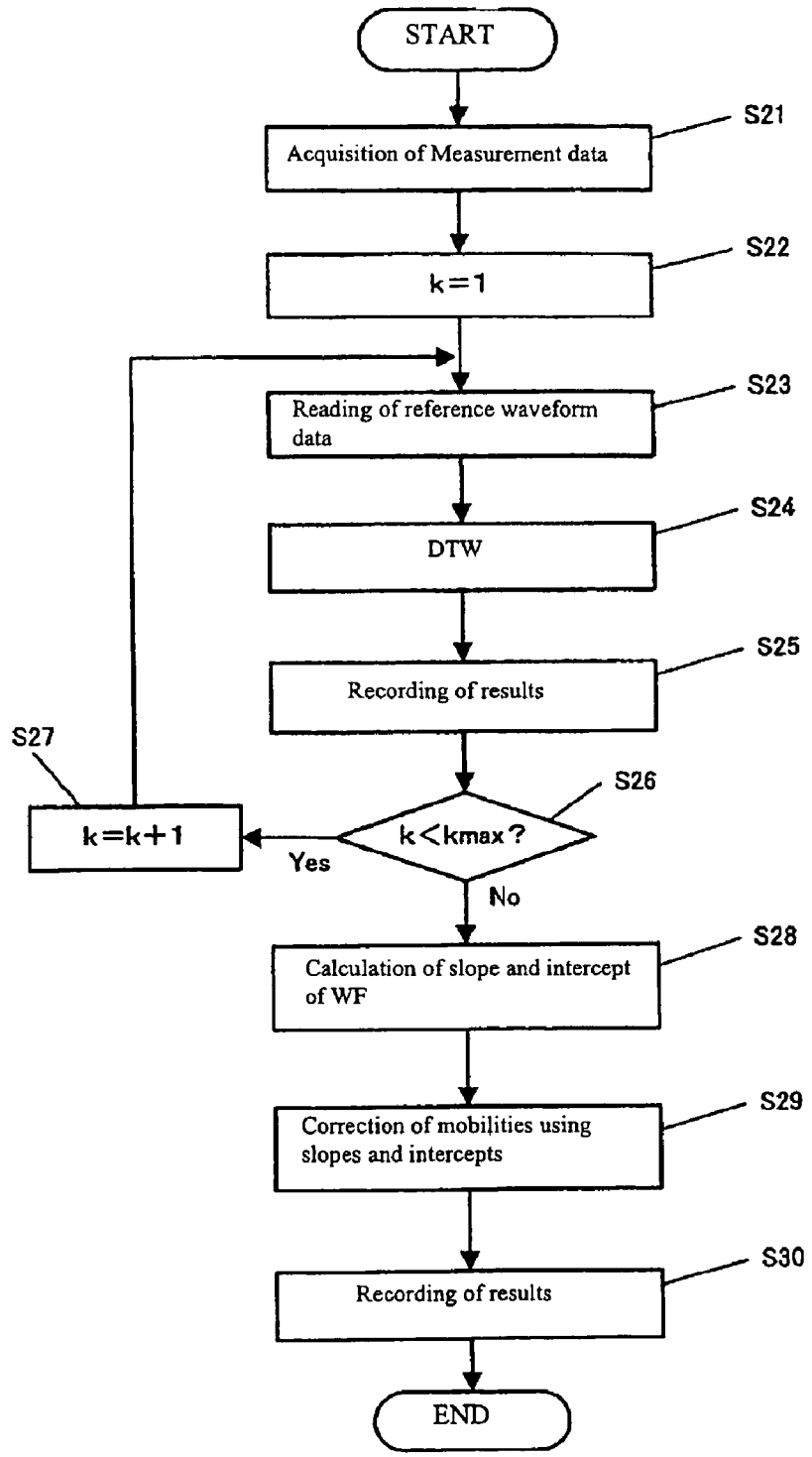
FIG. 5 is a flowchart showing the process to normalize mobilities, which is one of the processes performed by the test value prediction apparatus according to the embodiment of the present invention.

Next, an example of a method of normalizing measurement data obtained by the measuring apparatus (electrophoresis apparatus) 2 is described using the flowchart in FIG. 5. In the normalization method of the present invention, a process to obtain a warping function that converts measurement data to reference waveform data by DTW is carried out for a plurality of sets of measurement data, and slopes and intercepts of a plurality of warping functions thus obtained are used to normalize measurement data that is subject to normalization.

In Step S21, measurement data is acquired from the measuring apparatus via the communication IF unit 17 and recorded in the recording 13 unit. The measurement data is one-dimensional time series data measured at predetermined time intervals.

In Step S22, a counter k for counting repeated processes is set to 1.

In Step S23, one of a plurality of sets of reference waveform data recorded in advance is read from the recording unit 13.

Figure 6:
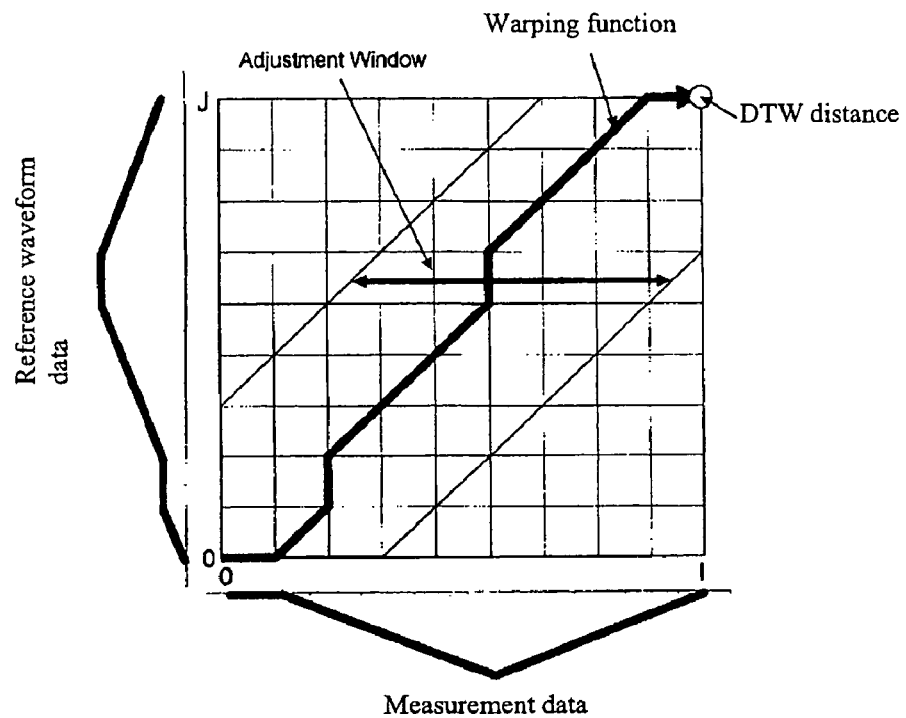
FIG. 6 shows the concept of DTW.

In Step S24, dynamic time warping (DTW) is applied to the reference waveform data read in Step S23 and the measurement data. More specifically, a warping function (hereinafter also referred to as a "WF") that converts measurement data to reference waveform data is determined, and then a DTW distance, which is a distance along the WF, is determined. Since DTW is a well-known process, the concept of DTW is shown in FIG. 6, with a detailed explanation being omitted. In FIG. 6, positive integer values are sequentially assigned to one set of unit time sequence data. The reference waveform data is assigned 0 to J, and the measurement data is assigned 0 to I.

In Step S25, the arithmetic processing unit 11 records the WF and the DTW distance determined in Step S24 in the recording unit 13 in a manner such that the WF and the DTW distance are associated with the reference waveform data. In this embodiment, as shown in FIG. 6, since the WF draws a polygonal line graph on a two-dimensional plane, the coordinates (i, j) ($0 \leq i \leq I$, $0 \leq j \leq J$) at each folding point are recorded into the recording unit 13.

In Step S26, the arithmetic processing unit 11 determines whether the value of the counter k is smaller than the total number (kmax) of sets of reference waveform data or not, thereby determining whether the processes from Steps S23 to S25 have been completed for all the sets of reference waveform data. When k<kmax, there still remains one or more sets of reference waveform data to be processed, so that the arithmetic processing unit 11 proceeds to Step S27 to increase the counter k by one, and returns to Step S23. In this manner, the processes from Steps S23 to S25 are applied to all the sets of reference waveform data.

In Step S28, the arithmetic processing unit 11 determines the minimum value of the DTW distances recorded in the recording unit 13, reads a set of the coordinate data of a WF corresponding to the minimum value from the recording unit 13, and determines the slope α (primary coefficient) and intercept β (constant term) of a linear function for linear approximation of the WF. Since the WF is theoretically a straight line, linear regression or a non-parametric linear regression method (for example, the Passing-Bablock technique) can be employed.

Figure 7:
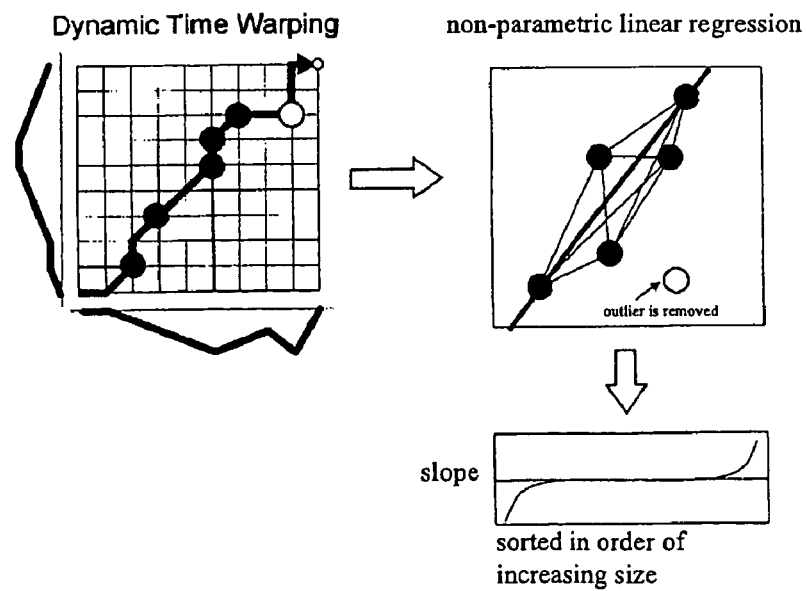
FIG. 7 shows the concept of the determination of the slope of a WF in a mobility normalization method.

In this normalization method of the present invention, any two sets of coordinate data are selected from a plurality of sets of coordinate data representing folding points on the WF read from the recording unit 13, and the slope of a straight line that passes through these two points is determined. The median of all the slopes is determined as the slope α of the straight line that approximates the WF. Similarly with respect to the intercept β, the intercepts of all the combinations are calculated, and the median of these values is determined as the intercept β of the straight line that approximates the WF. In this manner, both the slope α and the intercept β can be determined using the same non-parametric technique. FIG. 7 is a diagram that schematically illustrates this process. One diagram on the lower right of FIG. 7 is a graph in which slopes between points given by respective set of coordinate data are arranged in ascending order from the left. Although the line of this graph is substantially flat around the center, it abruptly changes at around the right and left ends. Slopes of these regions are determined using, among the sets of coordinate data representing folding points on the WF, sets of coordinate data representing folding points that greatly fall out of the straight line when the WF is linearly approximated. Thus, using the median of the slope distribution, outliers can be removed.

In Step S29, the measurement data to be normalized is corrected using the slope α and intercept β determined in Step S28. More specifically, using the value of i' determined in accordance with the equation, i'=α×i+β (wherein $0 \leq i \leq I$), the position of a mobility m(i) that comprises the measurement data on the graph is shifted to a new position i' from the position i. This means that the time axis of the measurement data is scaled (extended or shortened) and offset.

In Step S30, the arithmetic processing unit 11 records the measurement data corrected in Step S29 in the recording unit 13, thereby completing the normalization process of the measurement data. By way of the aforementioned processes, it is possible to normalize (correct the time axis of) the measurement data on mobilities, using sets of reference waveform data that have been prepared in advance, without the use of a marker substance.

When applying the present normalization method to Step S2 above for calculation of a prediction value (see FIG. 2) and Step S12 above for generation of a prediction equation (see FIG. 3), the slope α and the intercept β determined in the above Step S28 in advance (see FIG. 5) simply should be recorded in the recording unit 13.

As can be understood from the explanation above, the accuracy of the normalization method depends upon the accuracy of the reference waveform data. When analyses involving markers are possible in some reference laboratories or the like, reference waveform data can be prepared by normalizing the mobilities measured using the marker information as in conventional manners.

In the case of an analysis method that cannot include a marker, the waveform data determined by self-organizing map (SOM) can be used as reference waveform data. Since SOM and the method of generating SOMs are well-known, a detailed explanation thereof is omitted; an example of an application of SOM to mobility measurement data is explained below.

First, from a plurality of sets of waveform data obtained using an analysis process that cannot include a marker, sets of representative waveform data are selected, and these sets of representative waveform data are visually corrected to provide sets of initial reference waveform data. Next, using these initial reference waveform data, clustering by SOM is performed to extract sets of typical waveform data. The resulting sets of extracted waveform data are the sets of reference waveform data for use in this embodiment.

Figure 8:
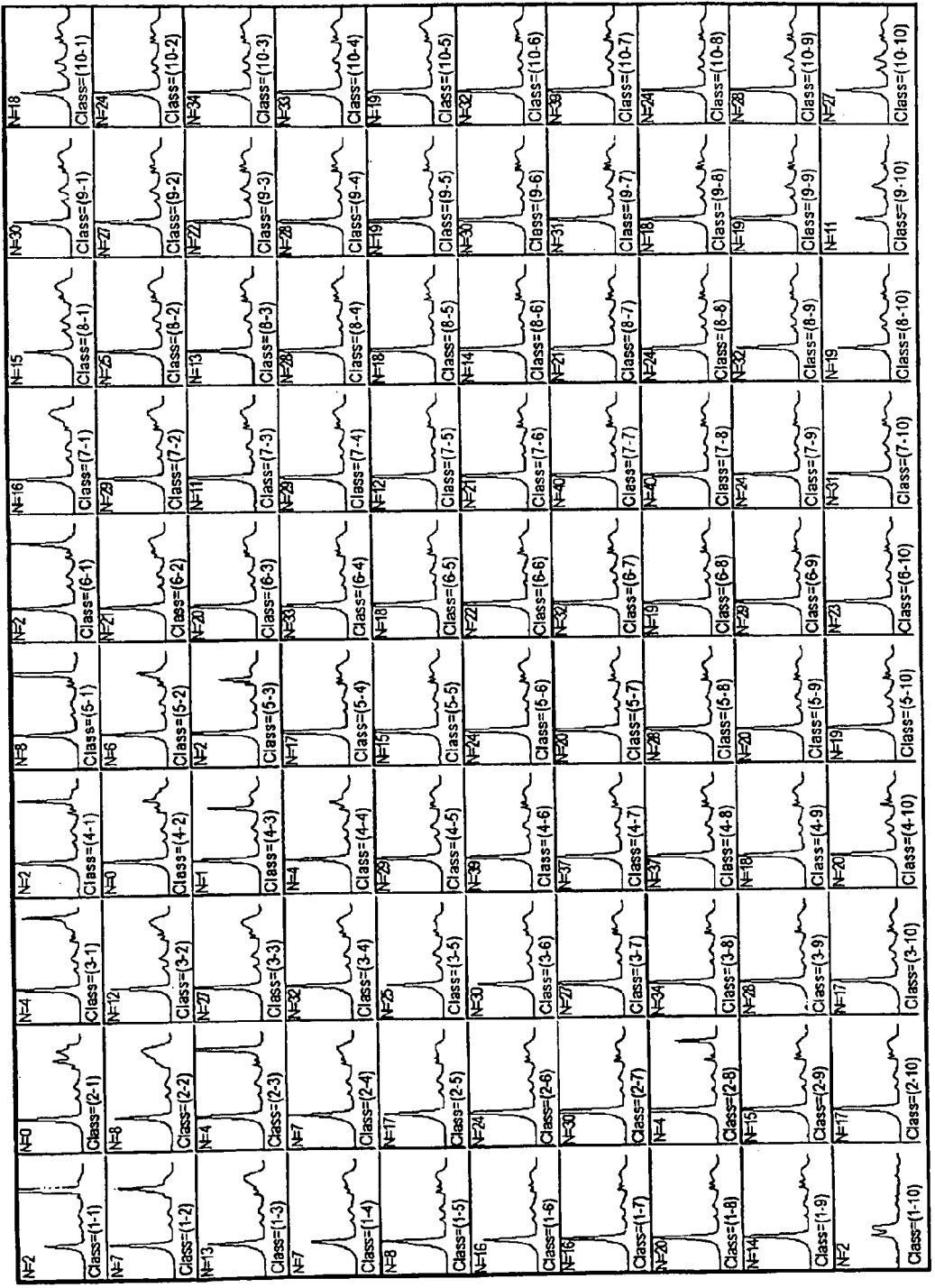
FIG. 8 is a diagram showing an example of an SOM obtained using sets of measurement data measured by capillary electrophoresis.

At this state, if sets of typical waveform data fail to be extracted by clustering using SOM, the above-described correction procedure can be repeated until sets of such data are extracted, thus generating sets of reference waveform data with high accuracy. FIG. 8 shows an example of reference waveform data obtained using measurement data determined by capillary electrophoresis. In FIG. 8, the SOM consists of one-hundred sets of reference waveform data. The correction accuracy can be enhanced by changing the number of sets of reference waveform data according to the type of the waveform data for the target area.

The flowchart shown in FIG. 5 is merely an example, and does not limit the present invention. For example, although FIG. 5 illustrates a case in which DTW is applied to each set of reference waveform data, and all the results are recorded in the recording unit, the present invention is not limited to this example: any other process may be used insofar as the WF for the most approximate reference waveform data can be determined. Subsequent to the application of DTW on one set of reference waveform data, the result may be compared with a result of previous DTW on another reference waveform data, and only the WF of the smaller DTW distance (coordinate data representing folding points) may be stored.

In addition, although the case in which a WF is linearly approximated in Step S28 by using the medians of slopes and intercepts and removing the outliers was described above, the present invention is not limited to this example. For example, in the graph shown in FIG. 7, in which the slopes are sorted in order of increasing value, one value from the region with little fluctuation may be used, or the average value of the values in the region with little fluctuation may be used. The same applies to the intercepts.

Although the above description was directed to the case in which measurement data obtained by electrophoresis tests (such as capillary zone electrophoresis) is used, the present invention is not limited to the case above. Measurement data obtained by chromatography (liquid chromatography, gas chromatography, etc.) may also be used. Because a migration waveform similar to an electrophoresis waveform can be obtained from measurement data obtained by chromatography, the present invention is also applicable to chromatography measurement data instead of electrophoresis waveform data described above. Note that, in the case of liquid chromatography and gas chromatography, mobility is usually called retention time. This means that, in the present specification and the scope of claims, the term "mobility" means "retention time" in the case of liquid chromatography and gas chromatography.

Further, although the above description was directed to a case in which a test value at the time point when electrophoresis waveform data was measured is estimated from the measured data, a test value after a lapse of time can also be estimated. For example, in a diabetes test, a subject ingests a predetermined amount (for example, 75 g) of glucose, and then the temporal changes in the blood glucose level and the insulin level (for example, 30, 60, and 90 minutes after ingestion) are observed. The present invention is also applicable to such a diabetes test. In other words, the use of electrophoresis waveform data obtained by measuring the electrophoresis waveform of an analyte (blood) extracted immediately after ingestion of glucose allows predicting future values of the blood glucose level and the insulin level of the subject.

EXAMPLE 1

Examples are provided below to further clarify the characteristics of the present invention.

Figures 9, 10:
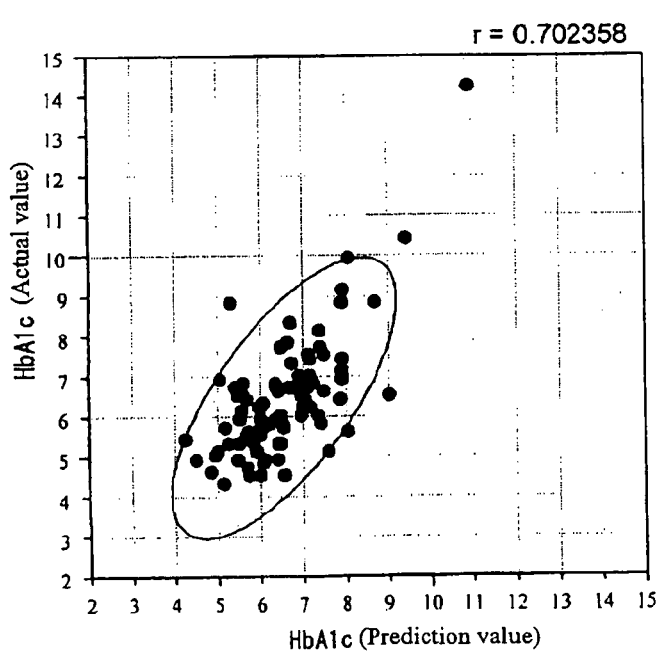
FIG. 9 is a diagram showing regression coefficients in tabular form, which were determined for HbA1c in accordance with the flowchart in FIG. 3.
FIG. 10 is a graph plotting the actual values of HbA1c and the prediction values thereof calculated using the regression coefficients in FIG. 9.

FIG. 9 is a diagram showing regression coefficients in tabular form, which were determined for HbA1c by performing a stepwise multiple regression analysis in accordance with the flowchart in FIG. 3.

First, 500 different analytes were subjected to the HbA1c test and the protein fractionation test that uses a capillary zone electrophoresis apparatus (CZE2000, Beckman Coulter). The obtained mobility waveform data was normalized using a self-organizing map and DTW such that the albumin peak is positioned at position 149 (associated with variable name "P149") and the marker peak is positioned at position 396 (associated with variable name "P396"), and the data was converted such that each waveform is presented by data consisting of 500 points (absorbance). Further, the area of the waveform was corrected using the total protein value. Then, using the obtained waveform data and the HbA1c values, the regression coefficients shown in FIG. 9 were determined by a stepwise multiple regression analysis.

FIG. 10 is a graph plotting the actual values of HbA1c and the prediction values thereof calculated using the regression coefficients in FIG. 9 (assuming that coefficients other than those shown in FIG. 9 are 0). The vertical axis represents the actual HbA1c values and the horizontal axis represents the prediction values, i.e., results obtained by calculating a prediction equation Y. The prediction values are calculation values for 100 analytes different from the 500 analytes used for the calculation of regression coefficients. The correlation coefficient between the prediction values and the actual values was 0.7. It is also clear from FIG. 10 that the prediction values satisfactorily reproduce the actual values.

Figure 11:
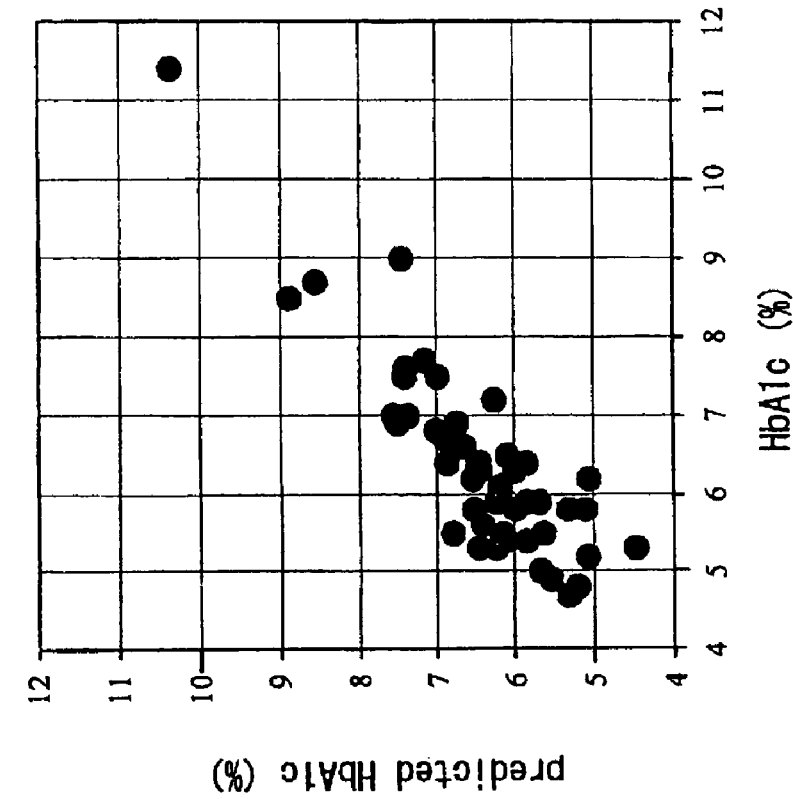
FIG. 11 shows the results of an analyte group different from that in FIGS. 9 and 10.

FIG. 11(a) shows regression coefficients determined in a similar manner as described above using a group of analytes different from that described above. Additionally, FIG. 11(b) is a diagram plotting the actual values and the prediction values calculated from the regression coefficients in FIG. 11(a), regarding 50 analytes. Note that, unlike FIG. 10, the vertical axis represents the prediction values and the horizontal axis represents the actual values. The correlation coefficient between the prediction values and the actual values was 0.78. Among the variable names shown in FIG. 11(a), variable names representing positive regression coefficients making a significant contribution are P28, P130, P261, P302, and P329, and variable names representing negative regression coefficients making a significant contribution are P138, P148, P258, and P419. In other words, the use of absorbance values corresponding to these variable names as explanatory variables in combination with a constant of order 0 allows a highly accurate estimation of a test value.

EXAMPLE 2

FIG. 12 is a diagram showing regression coefficients in tabular form, which were determined for HDL by performing a stepwise multiple regression analysis in accordance with the flowchart in FIG. 3, as is the case with Example 1.

Figure 13:
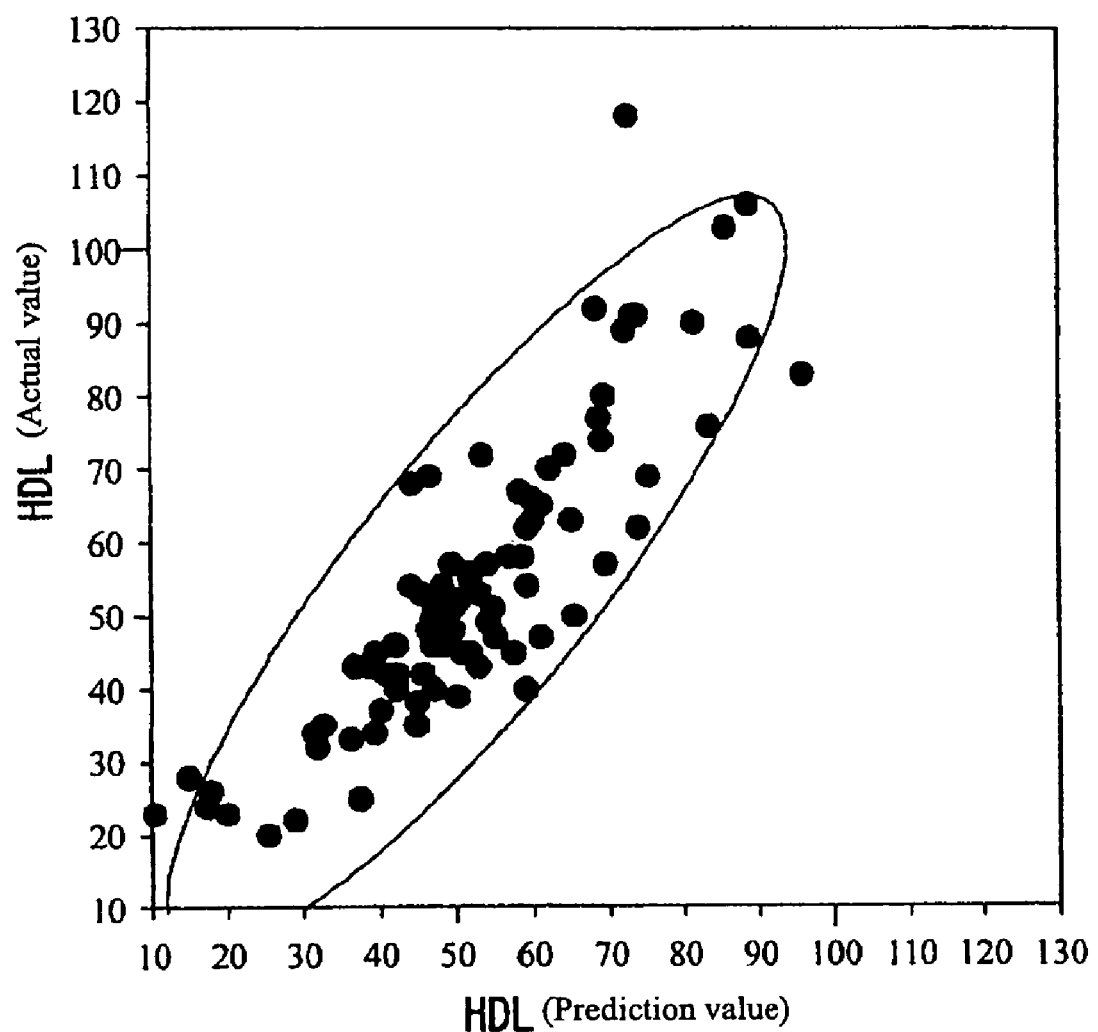
FIG. 13 is a graph plotting the actual values of HDL and the prediction values thereof calculated using the regression coefficients in FIG. 11.

FIG. 13 is a graph plotting the actual values of HDL and the prediction values thereof calculated using the regression coefficients in FIG. 12 (assuming that coefficients other than those shown in FIG. 12 are 0). The vertical axis represents the actual HDL values and the horizontal axis represents the prediction values, i.e., results obtained by calculating a prediction equation Y. The prediction values are calculation values for 100 analytes different from the 500 analytes used for the calculation of regression coefficients. The correlation coefficient between the prediction values and the actual values was 0.87. It is also clear from FIG. 13 that the prediction values satisfactorily reproduce the actual values.

Figure 14:
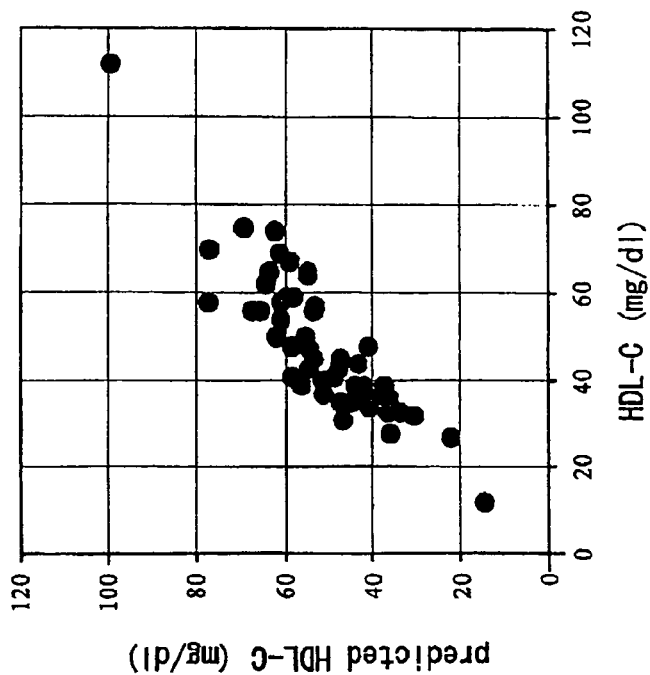
FIG. 14 shows results of an analyte group different from that in FIGS. 12 and 13.

FIG. 14(a) shows regression coefficients determined in a similar manner as described above using a group of analytes different from that described above. Additionally, FIG. 14(b) is a diagram plotting, as is the case with FIG. 13, the actual values and the prediction values calculated from the regression coefficients in FIG. 14(a), regarding 50 analytes. The vertical axis represents the prediction values and the horizontal axis represents the actual values. The correlation coefficient between the prediction values and the actual values was 0.82. Among the variable names shown in FIG. 14(a), a variable name representing a positive regression coefficient making a significant contribution is P189. In other words, the use of an absorbance value corresponding to this variable name as an explanatory variable in combination with a constant of order 0 allows a highly accurate estimation of a test value.

EXAMPLE 3

Figure 15:
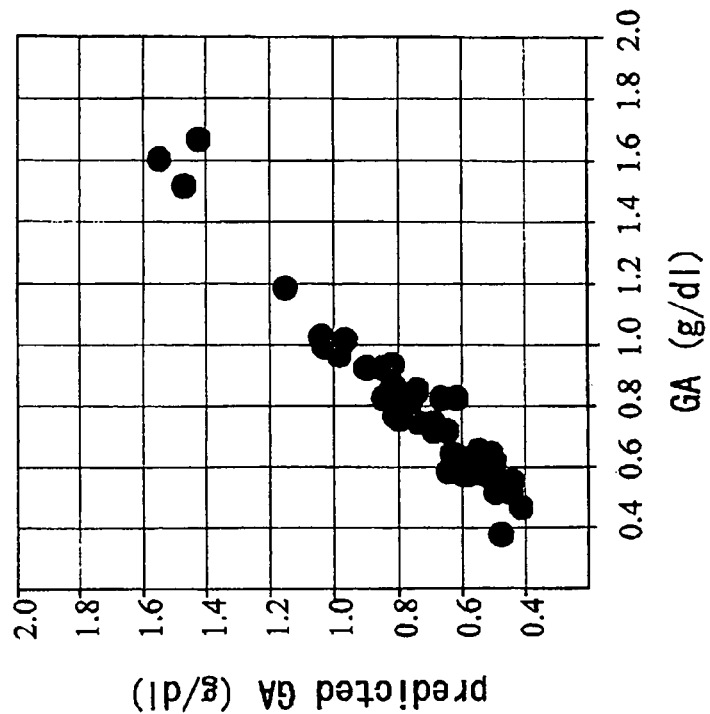
FIG. 15 shows Example regarding GA.

FIG. 15(a) is a diagram showing regression coefficients in tabular form, which were determined for glycoalbumin (GA) by performing a stepwise multiple regression analysis in accordance with the flowchart in FIG. 3, as is the case with Examples 1 and 2.

As described above, FIG. 15(b) is a graph plotting the actual values of GA and the prediction values thereof calculated using the regression coefficients in FIG. 15(a). The vertical axis represents the prediction values and the horizontal axis represents the actual values. The prediction values are calculation values of 50 analytes different from the 500 analytes used for the calculation of regression coefficients. The correlation coefficient between the prediction values and the actual values was 0.96. Among the variable names shown in FIG. 15(a), variable names representing positive regression coefficients making a significant contribution are P28, P128 and P347, and variable names representing negative regression coefficients making a significant contribution are P27, P31, P150 and P346. In other words, the use of absorbance values corresponding to these variable names as explanatory variables in combination with a constant of order 0 allows a highly accurate estimation of a test value.

EXAMPLE 4

Figure 16:
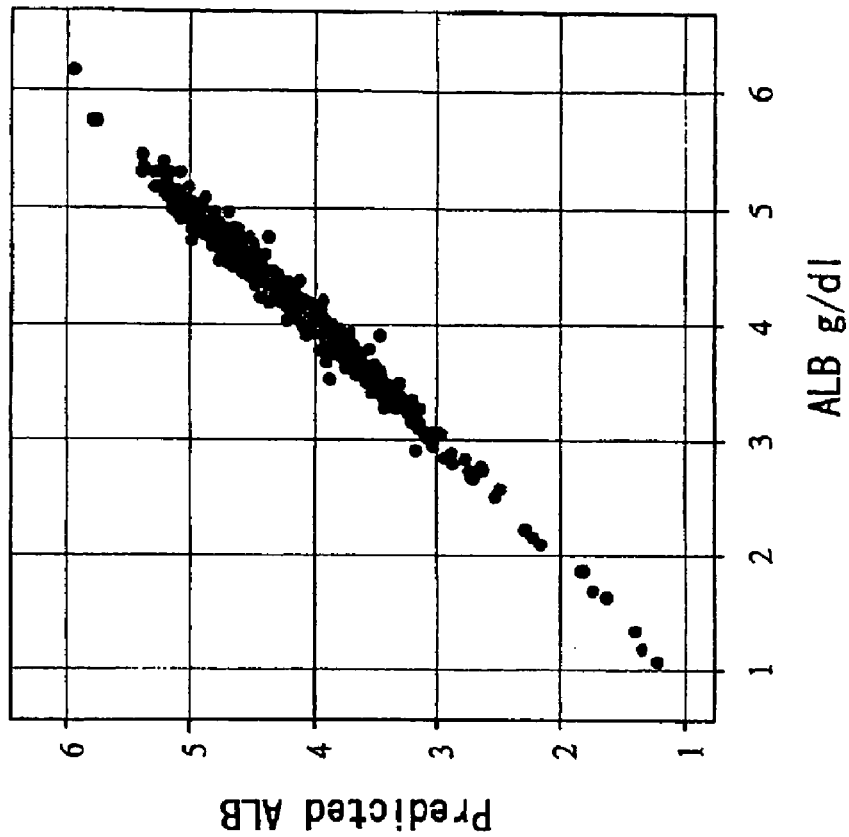
FIG. 16 shows Example in which a Gauss filter is applied.

For ALB (albumin), a convolution operation was performed on normalized waveform data, and the thus obtained waveform data was used to obtain a prediction equation. FIG. 16 shows the results. ALB is shown by the largest peak shape that appears to the left (in the vicinity of P149) of the electrophoresis waveform of ALB. A value of ALB can easily be obtained from the area under the curve of the waveform. However, the use of the estimation method of the present invention allows further accurate estimation by using waveforms multiplied by a Gaussian distribution curve at σ=7.8. In the case proteins present a clear fractionation, because the height of a specific position indicates the amount of pure protein, convolution using a Gaussian distribution curve can result in a reduction of the number of selected variable names and an improvement of the accuracy. FIG. 16(b) is a graph plotting, as in the case above, the actual values of ALB and the prediction values thereof calculated using the regression coefficient in FIG. 16(a). The vertical axis represents the prediction values and the horizontal axis represents the actual values. The correlation coefficient between the prediction values and the actual values was 0.99. Accordingly, it is clear that the prediction equation that uses the regression coefficient in FIG. 16(a) exhibits a high accuracy.

EXAMPLE 5

Using the presence or absence of a diagnosis of diabetes as learning data, an estimation parameter was determined by a multiple logistic regression analysis, and the actual diagnostic ability was examined. Specifically, using absorbance values corresponding to normalized mobilities as explanatory variables and the presence or absence of a disease as criterion variables ("1" for a person diagnosed as having the disease, and "0" for a person diagnosed as not having the disease), prediction parameters were determined by performing multiple logistic regression analysis, and a diagnosis of the disease was carried out based on these parameters.

Specifically the following equation was used.

Probability belonging to the disease group (diabetes) $=1/(1+e^{-X})$ $X=b0+b1 \times M1+b2 \times M2+ \ldots +bn \times Mn$ wherein, b0, b1, ..., bn are regression coefficients, M1, ..., Mn are absorbance values corresponding to mobilities indicated by variable names P001, ..., Pn.

Figure 17:
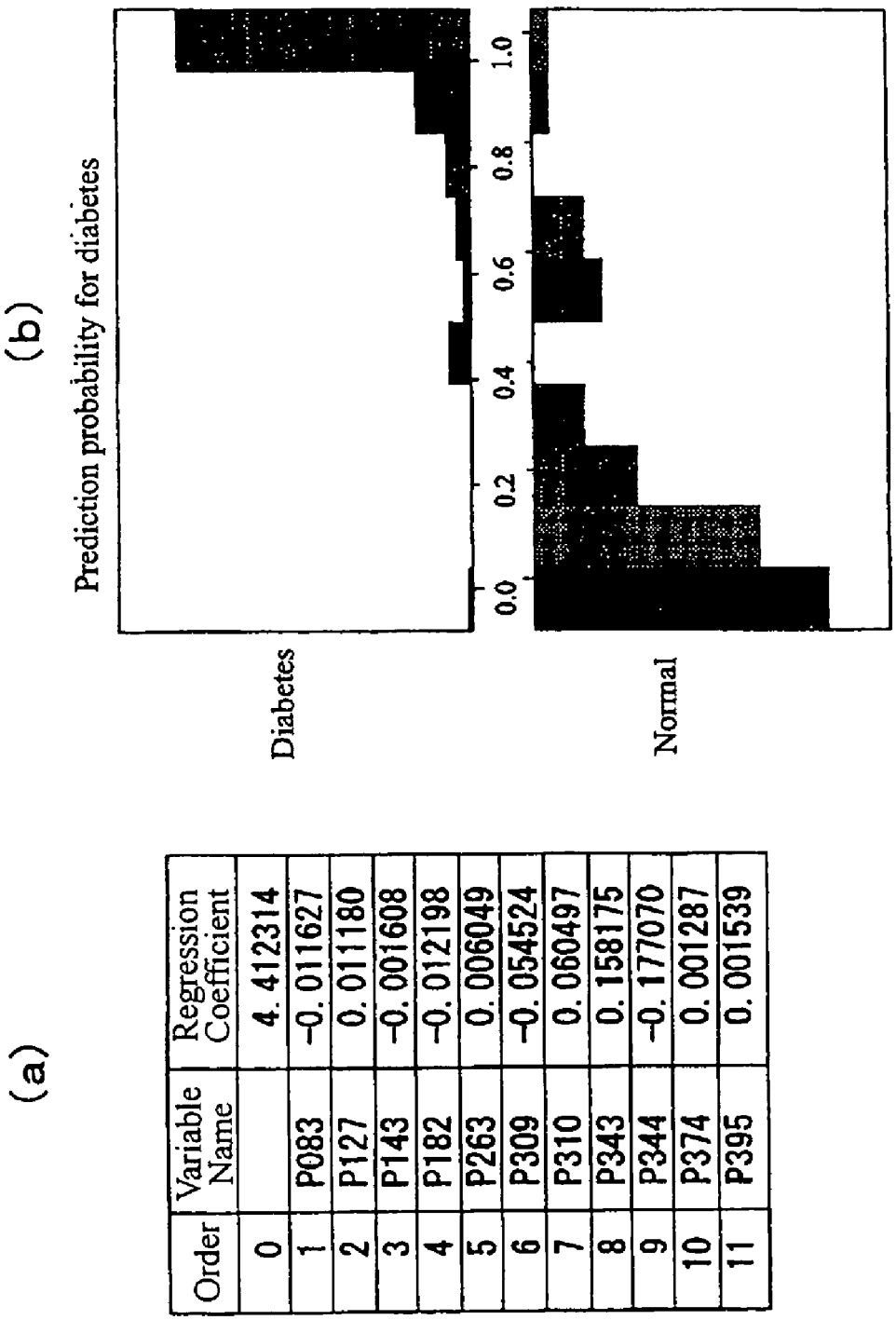
FIG. 17 shows Example which uses multiple logistic regression analysis.

FIG. 17 shows the results. FIG. 17(a) shows regression coefficients determined in a similar manner as described above. FIG. 17(b) shows prediction results calculated based on the regression coefficients in FIG. 17(a). In FIG. 17(b), the upper histogram shows a distribution of diabetic patients, and the lower histogram shows a distribution of non-diabetic patients. According to the results of prediction of a diabetic group, the test showed a high performance, with a sensitivity (percentage in which the presence of a diabetes was accurately identified by the diagnosis) of 94%, and a specificity (percentage in which the absence of a diabetes was accurately identified by the diagnosis) of 85.4%. These results are superior to evaluation results obtained by generally used single tests for HbA1c and GA.

INDUSTRIAL APPLICABILITY

The use of a regression equation obtained by a maximum likelihood estimation method in which normalized electrophoresis waveform data is used as an explanatory variable enables precise calculation of a test value that could not be predicted by a conventional protein fractionation test.

The invention claimed is:
1. A test value prediction apparatus comprising:
a recording unit and an operation unit, wherein
a mobility and an absorbance value corresponding to the mobility are used as a set of paired data; and electrophoresis waveform data formed by a plurality of said sets of paired data, and a prediction equation for predicting the amount of a specific substance in an analyte or the presence or absence of a disease in the living body from which the analyte was obtained are recorded in the recording unit;
the prediction equation is a regression equation predetermined by a maximum likelihood estimation method, in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;
the operation unit is configured to
read the electrophoresis waveform data recorded in the recording unit, and generate corrected waveform data by performing normalization and area correction on the electrophoresis waveform data, and
read the prediction equation recorded in the recording unit, calculate a value of the prediction equation by substituting the absorbance value corresponding to the mobility which is the explanatory variable of the prediction equation, with an absorbance value from the corrected waveform data generated from the electrophoresis waveform data recorded in the recording unit, and use the calculated value as a prediction value of the amount of the specific substance or the presence or absence of a disease; and the area correction is a process to correct absorbance values in electrophoresis waveform data using the area in the normalized electrophoresis waveform data and the total protein value of the analyte.

2. The test value prediction apparatus according claim 1, wherein the specific substance is one substance selected from the group consisting of hemoglobin A1c, glycoalbumin, HDL cholesterol, LDL cholesterol, total cholesterol, triglyceride, AFP, CEA, ALB, C4, transferrin, CRP, IgA, IgG, IgM, TP, CHE, GLB, ZTT, serum Ca, Na in urine, RBC, HT, HB, blood sedimentation, glucose in 24-hour collected urine, protein in 24-hour collected urine, 1.5-AG, anti-GAD Ab, circadian sugar level, blood sugar during glucose tolerance test (each hourly value), insulin during glucose tolerance test (each hourly value), lactate, pyruvic acid, sialic acid, hyaluronic acid, E-CHO, NEFA, H-CHO, TIBC, serum copper, zinc, vitamin B1, RBP, LCAT, lysozyme, CKMB (MB %, MM %), LH, FSH, prolactin, ACTH, T3, T4, CPR, insulin, BNP-FEI, FIB, lupus anti core grant, ASK, CH50, C3, LE, thyroid, anti-TG, anti-TPO, haptoglon, SAA, IAP, B2-MIC, NSE, HGF, P-3-P, collagen 7S, CA19-9R, CA72-4, BCA225, STN, pro-GRP, TPA, ELASTA, SPAN1, ICTP, PSA, ICG, ALB in urine, NAG in urine, and nasal fluid eosinophils.

3. The test value prediction apparatus according to claim 1, wherein the corrected waveform data used for determination of the prediction equation is waveform data obtained by performing convolution using Gaussian distribution on waveform data generated as a result of normalization of the electrophoresis waveform data on a plurality of analytes; and the operation unit normalizes the electrophoresis waveform data recorded in the recording unit, performs convolution using Gaussian distribution on the normalized waveform data, and generates the corrected waveform data used for calculation of the prediction value.

4. The test value prediction apparatus according to claim 1, wherein the specific substance is CEA; and the amount of the specific substance used as a criterion variable for determination of the prediction equation is a logarithmic value of a measured value of CEA.

5. The test value prediction apparatus according to claim 1, wherein the recording unit further records a first parameter and a second parameter that are used for normalization;

the operation unit normalizes the electrophoresis waveform data using a linear function in which the first parameter is a slope and the second parameter is an intercept;

a plurality of warping functions that convert the electrophoresis waveform data into a plurality of reference waveform data, and DTW distances corresponding the plurality of warping functions are obtained, and the first parameter is the slope of a straight line approximating the warping function that corresponds to the minimum DTW distance among the plurality of DTW distances, and the second parameter is the intercept of the straight line; and the slope of the straight line approximating the warping function is obtained by calculating slopes between any folding points of the warping function, excluding slopes included in predetermined regions at both ends when the plurality of slopes between folding points are arranged in order of value, and obtaining the slope of the straight line from the remaining slopes.

6. The test value prediction apparatus according to claim 1, wherein when the corrected waveform data is generated such that the albumin peak is at position 149 and the marker peak is at position 396, a prediction equation for hemoglobin A1c contains, as explanatory variables, absorbance values corresponding to mobilities at least at positions 28, 130, 138, 148, 258, 261, 302, 329, and 419, a prediction equation for HDL cholesterol contains, as an explanatory variable, an absorbance value corresponding to a mobility at least at position 189, or a prediction equation for glycoalbumin contains, as explanatory variables, absorbance values corresponding to mobilities at least at positions 27, 28, 31, 128, 150, 346, and 347.

7. A test value predicting method for predicting the amount of a specific substance in an analyte or the presence or absence of a disease in the living body from which the analyte was obtained, by using a computer comprising a recording unit and an operation unit, wherein a mobility and an absorbance value corresponding to the mobility are used as a set of paired data; and electrophoresis waveform data formed by a plurality of said sets of paired data, and a prediction equation for predicting the amount of a specific substance in an analyte or the presence or absence of a disease in the living body from which the analyte was obtained are recorded in the recording unit;

the prediction equation is a regression equation predetermined by maximum likelihood estimation method in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;

the test value prediction method further comprising:

a first step in which the operation unit reads the electrophoresis waveform data recorded in the recording unit, and generates corrected waveform data by performing normalization and area correction on the electrophoresis waveform data, and a second step in which the operation unit reads the prediction equation recorded in the recording unit, calculates a value of the prediction equation by substituting the absorbance value corresponding to the mobility which is the explanatory variable of the prediction equation with an absorbance value from the corrected waveform data generated from the electrophoresis waveform data recorded in the recording unit, and uses the calculated value as a prediction value of the amount of the specific substance or the presence or absence of a disease; and the area correction is a process to correct absorbance values in electrophoresis waveform data using the area in the normalized electrophoresis waveform data and the total protein value of the analyte.

8. The test value prediction method according to claim 7, wherein
the specific substance is one substance selected from the group consisting of hemoglobin A1c, glycoalbumin, HDL cholesterol, LDL cholesterol, total cholesterol, triglyceride, AFP, CEA, ALB, C4, transferrin, CRP, IgA, IgG, IgM, TP, CHE, GLB, ZTT, serum Ca, Na in urine, RBC, HT, HB, blood sedimentation, glucose in 24-hour collected urine, protein in 24-hour collected urine, 1.5-AG, anti-GAD Ab, circadian sugar level, blood sugar during glucose tolerance test (each hourly value), insulin during glucose tolerance test (each hourly value), lactate, pyruvic acid, sialic acid, hyaluronic acid, E-CHO, NEFA, H-CHO, TIBC, serum copper, zinc, vitamin B1, RBP, LCAT, lysozyme, CKMB (MB %, MM %), LH, FSH, prolactin, ACTH, T3, T4, CPR, insulin, BNP-FEI, FIB, lupus anti core grant, ASK, CH50, C3, LE, thyroid, anti-TG, anti-TPO, haptoglon, SAA, IAP, B2-MIC, NSE, HGF, P-3-P, collagen 7S, CA19-9R, CA72-4, BCA225, STN, pro-GRP, TPA, ELASTA, SPAN1, ICTP, PSA, ICG, ALB in urine, NAG in urine, and nasal fluid eosinophils.

9. The test value prediction method according to claim 7, wherein
the corrected waveform data used for determination of the prediction equation is waveform data obtained by performing convolution using Gaussian distribution on waveform data generated as a result of normalization of the electrophoresis waveform data on a plurality of analytes; and
in the second step, the operation unit normalizes the electrophoresis waveform data recorded in the recording unit, performs convolution using Gaussian distribution on the normalized wave form data, and generates the corrected waveform data used for calculation of the prediction value.

10. The test value prediction method according to claim 7, wherein
the specific substance is CEA; and
the amount of the specific substance used as the criterion variable for determination of the prediction equation is a logarithmic value of a measured value of CEA.

11. The test value prediction method according to claim 7, wherein
the recording unit further records a first parameter and a second parameter that are used for normalization;
in the first step, the operation unit normalizes the electrophoresis waveform data using a linear function in which the first parameter is a slope and the second parameter is an intercept;
a plurality of warping functions that convert the electrophoresis waveform data into a plurality of reference waveform data, and DTW distances corresponding the plurality of warping functions are obtained, and
the first parameter is the slope of a straight line approximating the warping function that corresponds to the minimum DTW distance among the plurality of DTW distances, and the second parameter is the intercept of the straight line; and
the slope of the straight line approximating the warping function is obtained by
calculating slopes between any folding points of the warping function,
excluding slopes included in predetermined regions at both ends when the plurality of slopes between folding points are arranged in order of value, and
obtaining the slope of the straight line from the remaining slopes.

12. The test value prediction method according to claim 7, wherein when the corrected waveform data is generated such that the albumin peak is at position 149 and the marker peak is at position 396,
a prediction equation for hemoglobin A1c contains, as explanatory variables, absorbance values corresponding to mobilities at least at positions 28, 130, 138, 148, 258, 261, 302, 329, and 419,
a prediction equation for HDL cholesterol contains, as an explanatory variable, an absorbance value corresponding to a mobility at least at position 189, or
a prediction equation for glycoalbumin contains, as explanatory variables, absorbance values corresponding to mobilities at least at positions 27, 28, 31, 128, 150, 346, and 347.

13. A test value prediction program, embedded in a non-transitory storage medium, for causing a computer comprising a recording unit and an operation unit to predict the amount of a specific substance in an analyte or the presence or absence of a disease in the living body from which the analyte was obtained, wherein
a mobility and an absorbance value corresponding to the mobility are used as a set of paired data; and electrophoresis waveform data formed by a plurality of said sets of paired data, and a prediction equation for predicting the amount of a specific substance in an analyte or the presence or absence of a disease in the living body from which the analyte was obtained are recorded in the recording unit;
the prediction equation is a regression equation predetermined by maximum likelihood estimation method in which the explanatory variable is an absorbance value corresponding to a mobility in corrected waveform data generated as a result of the electrophoresis waveform data on a plurality of analytes being subjected to normalization and area correction, and the criterion variable is the amount of the specific substance or the presence or absence of a disease;
the test value prediction program enabling
a first function in which the operation unit is caused to read the electrophoresis waveform data recorded in the recording unit and generate corrected waveform data by performing normalization and area correction on the electrophoresis waveform data, and
a second function in which the operation unit is caused to read the prediction equation recorded in the recording unit, calculate a value of the prediction equation by substituting the absorbance value corresponding to the mobility which is the explanatory variable of the prediction equation with an absorbance value from the corrected waveform data generated from the electrophoresis waveform data recorded in the recording unit, and use the calculated value as a prediction value of the amount of the specific substance; and
the area correction is a process to correct absorbance values in electrophoresis waveform data using the area in the normalized electrophoresis waveform data and the total protein value of the analyte.

* * * * *